United States Patent [19]

Rennie

[11] Patent Number: 4,466,973

[45] Date of Patent: Aug. 21, 1984

[54] METHOD OF TREATING NASAL AND SINUS CONGESTION

[76] Inventor: Thomas Rennie, Blackberry La., Bennington, Vt. 05201

[21] Appl. No.: 463,062

[22] Filed: Feb. 1, 1983

[51] Int. Cl.³ ............... A61K 31/165; A61K 31/245; A61K 31/445

[52] U.S. Cl. .................................... 424/267; 424/310; 424/324

[58] Field of Search ................ 424/324, 267, 310

[56] References Cited

U.S. PATENT DOCUMENTS

| | | | |
|---|---|---|---|
| 2,457,188 | 12/1948 | Stone | 167/52 |
| 2,741,574 | 4/1956 | Prindle | 167/58 |
| 3,244,588 | 4/1966 | Nielsen | 167/55 |
| 3,872,113 | 3/1975 | Fliedner, Jr. | 260/240 |
| 4,148,917 | 4/1979 | Smith | 424/310 |
| 4,337,270 | 6/1982 | Noda et al. | 424/310 |

OTHER PUBLICATIONS

"A Concept of Allergy As . . . An Improved Working Hypothesis", Henry L. Williams, M.D., Annals of Otology, Rhinology and Laryngology, vol. 60, pp. 122–151, Mar. 1951.

Koeddermann et al., Chemical Abstracts 78: 128425v (1973).

*Primary Examiner*—Leonard Schenkman
*Attorney, Agent, or Firm*—Harvey B. Jacobson

[57] ABSTRACT

A method for treating nasal congestion, sinus congestion, dysopthia and excessive lacrimation wherein an effective amount of a non-toxic topical anesthetic is applied to the palatal mucosa.

4 Claims, No Drawings

METHOD OF TREATING NASAL AND SINUS CONGESTION

BACKGROUND OF THE INVENTION

1. Field of the Invention

This invention is directed to a method for treating nasal congestion, sinus congestion, dysopthia, and excessive lacrimation whereby extended relief from said congestion is obtained.

2. Description of the Prior Art

Nasal and sinus congestion, stuffiness, dysophthia, and excessive lacrimation resulting from the common cold, as well as from reaction to various allergens, known as allergic rhinitis, is perhaps the most common medical problem, affecting essentially every person at one time or another in his life.

The physiological mechanism involved in allergic rhinitis is thought to be the result of arteriolar spasms, precipitated by reaction to the presence of antigenic material, which cause atonic dilation of the distal capillaries and venules of the peripheral vascular bed, thereby producing local cellular damage due to oxygen insufficiency and the concomitant release of histamines, which cause increased capillary permeability. This increased capillary permeability then results in additional edema or tissue necrosis and the cycle repeats itself.

Current medications available to treat the condition include various nasal sprays, oral medications and lozenges. The nasal sprays act to reduce the mucosal edema and have the extremely disadvantageous side effect that the body quickly develops a physiological dependence thereon, the result being that once a person becomes dependent on the nasal spray, he requires its use long after the original causation has disappeared. Therefore protracted use of the nasal sprays is discouraged to the point where the suggested duration of use does not provide the required relief.

The various oral medications available on the market generally contain an anti-histamine compound to counter-act the effects of the histamine-producing reaction. One difficulty with the use of these oral medications is that they are slow to produce a result, requiring absorbtion into the blood stream through the walls of the digestive tract, and transport to the situs by the blood stream, before their effects can begin to be experienced. Additionally, these oral medications produce undesirable side effects, drowsiness being one of the most noticeable.

As for the various lozenges, they are for the most part quite ineffective in producing any relief of the symptoms.

U.S. Pat. Nos. 2,457,188 and 2,741,574 show the use of benzocaine and procaine in pharmaceutically acceptable carriers. The references contain no suggestion of use for treatment of nasal and sinus congestion.

U.S. Pat. No. 3,244,588 illustrate the use of analgesics, similar in structure to benzocaine and procaine, as antitussives. This patent describes only that the compounds of the invention may be applied orally, but contains no details of the form used for application. Oral or parenteral administration is disclosed at col. 1, line 64. Logenzes and gums are disclosed at col. 3, lines 43–45.

U.S. Pat. No. 3,872,113 describes certain compounds, known to be analgesics, that are described as having immunosuppressive behavior. Immunosuppressive behavior is generally associated with treatment of allergies. Dosage forms are disclosed at col. 3, lines 51–53. The reference does not suggest the method of treatment of this invention.

U.S. Pat. No. 4,148,917 describes analgesic compounds that are used for various reasons. Relief of congestion is not specifically described. Also, it is described that the compounds of the invention are applied topically in a carrier that facilitates absorbtion through the skin. See column 15. A sugar ester is an essential ingredient of these compositions.

U.S. Pat. No. 4,337,220 describes compounds that are used for their anti-allergy activity, that are administered orally. There is no suggestion that these compounds might be used in the method of this invention.

Russian Pat. No. 511,948 teaches a method of treating bronchial asthma by injecting novocain into the costal cannal. Again, there is no suggestion that these compounds be used in the method of this invention.

Therefore a need has continued to exist for a method of treating nasal and sinus congestion which is safe, effective, long lasting, non-habit forming, achieves its result in a very short time after treatment begins, and easy to apply.

SUMMARY OF THE INVENTION

It is an object of this invention to provide a method for treating nasal and sinus congestion. It is a further object of this invention to provide a method for the treatment of nasal and sinus congestion which is safe and non-habit forming. It is yet a further object of this invention to provide a method for the treatment of sinus congestion which is easy to apply and produces a result in a very short time after treatment is begun. These and other objects of the invention, as will hereinafter become more readily apparent, have been accomplished by a method of treatment comprising application of an effective amount of a topical anesthetic to the palatal mucosa.

DESCRIPTION OF THE PREFERRED EMBODIMENT

In the practice of this invention, a topical anesthetic is applied to the palatal mucosa by suitable means. More specifically, the topical anesthetic is applied to the palatal mucosa in the area of the greater palatine foramena, the inferior openings of the greater palatine canal which are located laterally on the horizontal plate of each palatine bone opposite the root of each third molar tooth. More specifically yet, the topical application is made to the incisive papilla, the tiny ridge which exists just behind the maxillary incisors.

This application of the topical anesthetic has the effect of anesthetizing the anterior palatine nerve which traverses each side of the nasal septum prior to passing through the anterior palatine foramen to terminate the incisive papilla. The result of this application of topical anesthetic to the palatal mucosa at the areas of the bilateral greater palatine foramena and the incisive papilla, and the accompanying anesthetization of the anterior palatine nerve is a reduction of edema of the nasal and sinus mucosa and a marked reduction in the feeling of sinus and nasal pressure and congestion. Additionally shrinkage of the swollen musoca in the area of the sinus ostia permits the sinus secretions to drain through the external nares.

It is hypothesized that application of a topical anesthetic to the distal end of the paranasal sensory nerves result in a reflex relief of edema and congestion by relieving the arteriolar and venular spasming in the nasal mucosa, thereby interrupting the cycle of cellular damage and release of histamines described above.

Suitable topical anesthetics for the practice of this invention are all those topical anesthetics which are not toxic to the human system. Representative examples include, but are not limited to, lidocaine, benzocaine, procaine and bupivacaine HCL. Preferred topical anesthetics are lidocaine and benzocaine.

The amount of topical anesthetic required for the practice of this invention is that amount necessary to effect anesthetization of the anterior palatine nerves traversing each side of the nasal system. Typically, an amount equal to about the size of a wooden match head will suffice, but greater or lesser amounts are within the contemplation of the inventor.

The method of application of the topical anesthetic include all methods effective in transferring the topical anesthetic to the desired area. Suitable methods of application include, but are not limited to, application with a cotton-tipped applicator, or a clean finger tip. In one embodiment of this invention, the topical anesthetic is combined with Orabase, a carboxymethylcellulose gel prepared by Hoyt Laboratories which forms a thin tenacious film on oral mucosa.

Another suitable method of application involves drying the mucosa with gauze and then applying the topical anesthetic with a suitable applicator, followed by covering the site of application with a gauze for a brief period. The materials for using the method of the present invention can be packaged in a kit for relief of nasal and sinus congestion which contains an applicator, a topical anesthetic in an amount sufficient to relieve nasal congestion, sinus congestion or both, in an air tight package.

However, due to the tendency of saliva to dilute the medication, rinses, sprays and troches are contraindicated.

The method of this invention is suitable for relief of nasal and sinus congestion which are the result of specific upper respiratory infections such as colds, influenzas and viruses as well as allergy-related symptoms. Relief is provided for essentially any and all allergic rhinitis and upper respiratory rhinitis.

Dramatic improvement is noted almost immediately, usually within five minutes and may last for periods of two to three hours to up to two days.

The invention now being fully described, it will be apparent to one with ordinary skill in the art that many changes and modifications can be made thereto without departing from the spirit or scope of the invention as set forth herein.

What is claimed is:

1. A method of treating nasal congestion, sinus congestion, dysophthia, and excessive lacrimation comprising applying an effective amount of a topical anesthetic to the palatal mucosa of a subject suffering therefrom.

2. The method of claim 1 which further comprises applying said topical anesthetic to the incisive papilla.

3. The method of claim 1 wherein the topical anesthetic is selected from the group consisting of lidocaine, benzocaine, procaine, and bupivacaine HCl.

4. The method of claim 1 wherein the topical anesthetic is applied in an amount sufficient to effect a reduction in nasal congestion, sinus congestion or both.

* * * * *